United States Patent
Govari et al.

(10) Patent No.: US 10,646,197 B2
(45) Date of Patent: May 12, 2020

(54) ASCERTAINING TISSUE THICKNESS

(71) Applicant: BIOSENSE WEBSTER (ISRAEL) LTD., Yokneam (IL)

(72) Inventors: Assaf Govari, Haifa (IL); Andres Altmann, Haifa (IL); Dmitry Volkinshtein, Zichron Yaakov (IL)

(73) Assignee: Biosense Webster (Israel) Ltd., Tokneam (IL)

( * ) Notice: Subject to any disclaimer, the term of this patent is extended or adjusted under 35 U.S.C. 154(b) by 415 days.

(21) Appl. No.: 15/202,979

(22) Filed: Jul. 6, 2016

(65) Prior Publication Data
US 2018/0008229 A1  Jan. 11, 2018

(51) Int. Cl.
| | | |
|---|---|---|
| A61B 8/08 | (2006.01) | |
| A61B 8/12 | (2006.01) | |
| A61B 8/00 | (2006.01) | |
| A61B 18/14 | (2006.01) | |
| A61B 90/00 | (2016.01) | |
| A61B 17/00 | (2006.01) | |
| A61B 18/00 | (2006.01) | |

(52) U.S. Cl.
CPC .............. *A61B 8/0858* (2013.01); *A61B 8/12* (2013.01); *A61B 8/429* (2013.01); *A61B 8/5223* (2013.01); *A61B 18/1492* (2013.01); *A61B 8/085* (2013.01); *A61B 8/0883* (2013.01); *A61B 2017/00106* (2013.01); *A61B 2018/00351* (2013.01); *A61B 2018/00577* (2013.01); *A61B 2018/00702* (2013.01); *A61B 2018/00761* (2013.01); *A61B 2090/065* (2016.02)

(58) Field of Classification Search
CPC ... A61B 8/0858; A61B 18/1492; A61B 8/429; A61B 8/12; A61B 8/5223; A61B 2018/00577; A61B 2018/00761; A61B 2017/00106; A61B 2090/065; A61B 2018/00702; A61B 2018/00351; A61B 8/085; A61B 8/0883
USPC ................................................. 600/437–469
See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,554,774 B1 | 4/2003 | Miele |
| 6,569,098 B2 | 5/2003 | Kawchuk |
| 6,814,733 B2 | 11/2004 | Schwartz et al. |

(Continued)

FOREIGN PATENT DOCUMENTS

| | | |
|---|---|---|
| WO | WO 2014/097014 A1 | 6/2014 |
| WO | WO 2015/113813 A1 | 8/2015 |

OTHER PUBLICATIONS

European Search Report dated Dec. 8, 2017 from corresponding European Patent Application No. 17179741.8.

*Primary Examiner* — Sanjay Cattungal

(57) ABSTRACT

Embodiments described herein include apparatus that includes an electrical interface and a processor. The processor is configured to receive, via the electrical interface, a first signal that indicates a time-varying force that was applied to a portion of tissue, and one or more second signals that are derived from ultrasound reflections received from the portion of tissue. The processor is further configured to learn, from the first signal and the second signals, a dependency of a thickness of the portion of tissue on the force applied to the portion of tissue. Other embodiments are also described.

20 Claims, 2 Drawing Sheets

(56) References Cited

U.S. PATENT DOCUMENTS

| | | |
|---|---|---|
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,517,318 B2 | 10/2009 | Altmann et al. |
| 7,604,601 B2 | 10/2009 | Altmann et al. |
| 7,756,576 B2 | 7/2010 | Levin |
| 7,877,128 B2 | 1/2011 | Schwartz |
| 8,317,711 B2 | 11/2012 | Dala-Krishna |
| 8,320,711 B2 | 11/2012 | Altmann et al. |
| 8,456,182 B2 | 6/2013 | Bar-Tal et al. |
| 8,545,408 B2 | 10/2013 | Sliwa et al. |
| 8,562,546 B2 | 10/2013 | Shih et al. |
| 8,583,220 B2 | 11/2013 | Schwartz |
| 8,628,473 B2 | 1/2014 | Sliwa et al. |
| 2007/0083193 A1* | 4/2007 | Werneth ............... A61B 5/7445 606/41 |
| 2007/0106156 A1* | 5/2007 | Altmann ............... A61B 8/12 600/437 |
| 2008/0178654 A1* | 7/2008 | Hochmitz ............ A61B 5/061 73/1.85 |
| 2008/0183075 A1* | 7/2008 | Govari ............... A61B 8/12 600/437 |
| 2009/0093806 A1 | 4/2009 | Govari et al. |
| 2009/0143677 A1* | 6/2009 | Govari ............... A61B 8/0883 600/439 |
| 2011/0028848 A1 | 2/2011 | Shaquer et al. |
| 2011/0144491 A1 | 6/2011 | Sliwa et al. |
| 2011/0160596 A1* | 6/2011 | Cecere ............... A61B 5/029 600/481 |
| 2012/0165671 A1* | 6/2012 | Hill ................. A61B 8/0883 600/443 |
| 2012/0165672 A1* | 6/2012 | Hill ................. A61B 8/463 600/443 |
| 2012/0259194 A1 | 10/2012 | Selkee |
| 2013/0123629 A1 | 5/2013 | Rosenberg et al. |
| 2013/0338477 A1* | 12/2013 | Glossop ............ A61B 10/0241 600/407 |
| 2014/0081262 A1 | 3/2014 | Koblish et al. |
| 2014/0094701 A1 | 4/2014 | Kwartowitz et al. |
| 2014/0100563 A1 | 4/2014 | Govari et al. |
| 2014/0142438 A1* | 5/2014 | Ludwin ............... A61B 5/1076 600/481 |
| 2015/0018679 A1* | 1/2015 | Endo ................. A61B 8/485 600/438 |
| 2016/0097716 A1* | 4/2016 | Gulati ............... A61B 5/02416 250/339.01 |
| 2016/0183915 A1 | 6/2016 | Govari et al. |
| 2018/0008229 A1* | 1/2018 | Govari ............... A61B 8/12 |
| 2018/0146953 A1* | 5/2018 | Jaremko ............. A61B 8/0875 |

* cited by examiner

ASCERTAINING TISSUE THICKNESS

FIELD OF THE INVENTION

Embodiments of the present invention relate to ultrasound imaging and to ablation procedures, especially as pertains to the heart.

BACKGROUND

US Patent Application Publication 2016/0183915, whose disclosure is incorporated herein by reference, describes determining wall thickness of a cavity by inserting a catheter into contact with a wall of a cavity in a body of a subject. The distal segment of the catheter is provided with a contact force sensor and an ultrasound transducer. The transducer is actuated to acquire ultrasound reflection data from the wall of the cavity, and while the transducer is actuated, the catheter is reciprocated against the wall of the cavity and the contact force measured between the catheter and the wall of the cavity. The reflection data is correlated with the contact force. A set of the correlated reflection data having the highest correlation with the contact force is identified. The tissue thickness between the inner surface and the identified set of the reflection data is calculated according to the time-of-flight therebetween.

US Patent Application Publication 2009/0093806, whose disclosure is incorporated herein by reference, describes a medical probe that includes a flexible insertion tube, having a distal end for insertion into a body cavity of a patient, and a distal tip, which is disposed at the distal end of the insertion tube and is configured to be brought into contact with tissue in the body cavity. A resilient member couples the distal tip to the distal end of the insertion tube and is configured to deform in response to pressure exerted on the distal tip when the distal tip engages the tissue. A position sensor within the probe senses a position of the distal tip relative to the distal end of the insertion tube, which changes in response to deformation of the resilient member.

US Patent Application Publication 2011/0028848, whose disclosure is incorporated herein by reference, describes a device for measuring a spatial location of a tissue surface, such as the interface between different types of tissues or between tissue and body fluids, which generally includes an elongate catheter body having a distal end portion, a plurality of localization elements carried by the distal end portion, and at least one pulse-echo acoustic element carried by the distal end portion. The localization elements allow the catheter to be localized (e.g., position and/or orientation) within a localization field, while the acoustic element allows for the detection of tissue surfaces where incoming acoustic energy will reflect towards the acoustic element. A suitable controller can determine the location of the detected tissue surface from the localization of the distal end portion of the catheter body. Tissue thicknesses can be derived from the detected locations of multiple (e.g., near and far) tissue surfaces. Maps and models of tissue thickness can also be generated.

US Patent Application Publication 2014/0081262, whose disclosure is incorporated herein by reference, describes various embodiments that concern delivering an ablation therapy to different areas of the cardiac tissue and, for each of the areas, sensing an ultrasound signal with at least one ultrasound sensor, the ultrasound signal responsive to the ultrasound energy reflected from the area of cardiac tissue. Such embodiments can further include for each of the plurality of different areas of the cardiac tissue, associating with each area an indication of the degree to which the area of cardiac tissue was lesioned by the delivery of the ablation therapy based on the ultrasound signal and representing a map of the different areas on a display. A user input can select one of the different areas and the indication associated with the selected one area can be represented on the map.

U.S. Pat. No. 8,317,711, whose disclosure is incorporated herein by reference, describes a dynamic ultrasound image catheter that includes a catheter body with an acoustic window on the distal end, an ultrasound phased array transducer assembly configured to rotate within the acoustic window through an angle of rotation, an acoustic coupling fluid filling a gap between the transducer array and the acoustic window, and a drive motor at the proximal end of the catheter body that is configured to rotate the transducer array. The drive motor may transmit a rotational force to the ultrasound phased array transducer by a drive wire or by tension wires coupled to drive spools. A system processor coupled to the drive motor controls rotation of the transducer array and estimates the angular orientation of the transducer array. By taking ultrasound images at increments through the angle of rotation, the dynamic ultrasound image catheter can obtain images spanning a volume which can be processed to generate three-dimensional composite images.

PCT International Publication WO/2014/097014, whose disclosure is incorporated herein by reference, describes a tracking, and point-of-view-based imaging, device that is configured for deriving a position of, and a direction from, a location at a distal tip of an elongated instrument, for performing coordinate system transformation in accordance with the position and direction, and for forming, from the location and based on a result of the transformation, a local view that moves with the tip. The device can keep, with the movement, a field of view of the local view fixed but the local view otherwise in synchrony with the position and the direction. From real-time ultrasound imaging, the local view and a more overall view that includes the tip but which does not move with said tip can be displayed. The distal tip can be that of a catheter and can be outfitted with a micromanipulator for surgery aided interactively by the combination of dynamic local and overall imaging.

U.S. Pat. No. 8,562,546, whose disclosure is incorporated herein by reference, describes a sensor system for measuring an elastic modulus and a shear modulus and a method for using the sensor system to evaluate a tissue by determining the presence of and/or characterizing abnormal growths. The method involves applying a set of forces of different magnitudes to one or more locations of tissue, detecting the corresponding displacements due to said applied forces, determining the forces acting on those locations of tissue which are a combination of forces from the applied voltages and the countering forces from tissue deformation, obtaining the elastic modulus and/or shear modulus for a plurality of locations, and determining abnormal growth invasiveness, malignancy or the presence of a tumor from said elastic and/or shear moduli.

SUMMARY OF THE INVENTION

There is provided, in accordance with some embodiments of the present invention, apparatus that includes an electrical interface and a processor. The processor is configured to receive, via the electrical interface, a first signal that indicates a time-varying force that was applied to a portion of tissue, and one or more second signals that are derived from ultrasound reflections received from the portion of tissue. The processor is further configured to learn, from the first signal and the second signals, a dependency of a thickness of the portion of tissue on the force applied to the portion of tissue.

In some embodiments, the processor is further configured to generate, based on the learned dependency, an output indicating at least one recommended parameter for an ablation of the portion of tissue performed at a particular contact force.

In some embodiments, the processor is configured to generate the output by:

based on the learned dependency, estimating a thickness of the portion of tissue that would result from the particular contact force being applied to the portion of tissue during the ablation of the portion of tissue, and in response to the estimated thickness, generating the output.

In some embodiments, the recommended parameter includes a power of an ablating signal.

In some embodiments, the recommended parameter includes a duration of an ablating signal.

In some embodiments, the processor is further configured to set, based on the learned dependency, at least one parameter for an ablation of the portion of tissue.

In some embodiments, the portion of tissue is a portion of cardiac tissue.

In some embodiments, the time-varying force was applied to the portion of tissue by a distal end of a catheter.

In some embodiments, the ultrasound reflections were received by an ultrasound transducer disposed within the distal end of the catheter.

In some embodiments, the processor is further configured:

to ascertain, based on a direction of the time-varying force during a first period of time during which the first signal was acquired, that ultrasound reflections received during the first period of time were not reflected from the portion of tissue, and in response thereto, to select, as the one or more second signals, one or more signals that are derived from ultrasound reflections received during a second period of time that is different from the first period of time.

There is further provided, in accordance with some embodiments of the present invention, a method that includes receiving a first signal that indicates a time-varying force that was applied to a portion of tissue, and one or more second signals that are derived from ultrasound reflections received from the portion of tissue. The method further includes learning, from the first signal and the second signals, a dependency of a thickness of the portion of tissue on the force applied to the portion of tissue, and generating an output that is based on the learned dependency.

The present invention will be more fully understood from the following detailed description of embodiments thereof, taken together with the drawings, in which:

DETAILED DESCRIPTION OF EMBODIMENTS

Overview

When performing an ablation of tissue, it is often helpful to know the thickness of the tissue, such that the parameters of the ablating signal may be appropriately set. One option for measuring tissue thickness is to use ultrasound imaging. For example, to prepare for a cardiac ablation, an ultrasound transducer inside the heart may transmit ultrasound signals into the cardiac tissue, and the tissue thickness may be ascertained from the times-of-flight of the reflections of these signals.

A challenge with the above-described method is that the thickness of the cardiac tissue may vary with the mechanical force (or equivalently, mechanical pressure) that is applied to the tissue by the ablation electrode. Embodiments of the present invention address this challenge, by using a signal from a force sensor to learn the dependency of the tissue thickness on the force that is applied to the tissue. In other words, the signal from the force sensor is used to express the tissue thickness as a function of the applied force. Subsequently, the tissue thickness that would result from the desired ablation contact force is estimated, and the other ablation parameters are then set accordingly.

In embodiments of the present invention, a catheter is inserted into the heart of a subject. The distal end of the catheter comprises an ablation electrode for ablating cardiac tissue, a force sensor, and an ultrasound transducer. As the physician moves the distal end of the catheter along the tissue of the heart, the force sensor measures the force applied to the tissue by the distal end, and the ultrasound transducer records ultrasound reflections from the tissue. A processor receives signals from the force sensor and the ultrasound transducer, and, using the signals, learns the dependency of the tissue thickness on the applied force.

System Description

Figure 1:
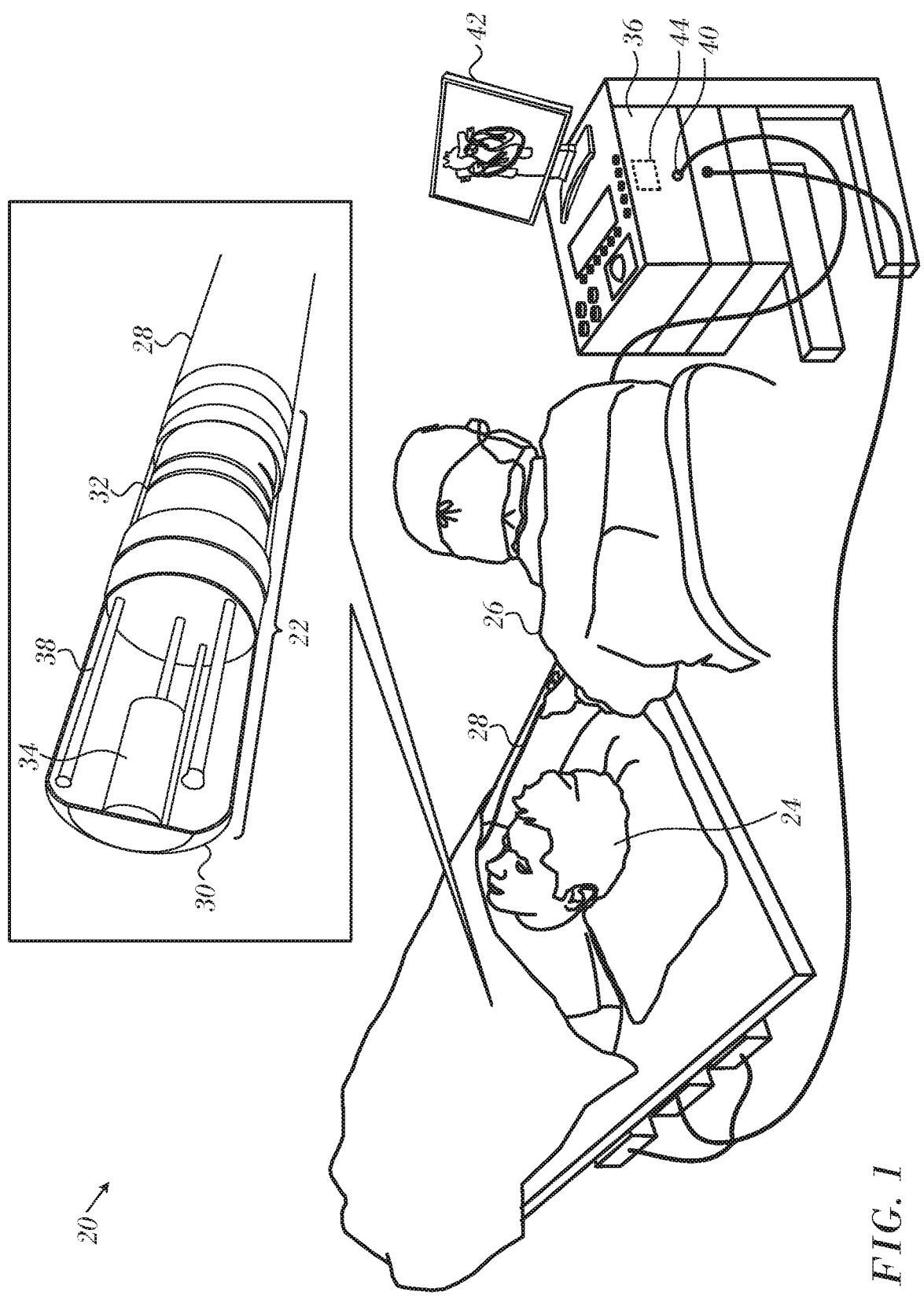
FIG. 1 is a schematic illustration of a system for performing a cardiac ablation, in accordance with some embodiments of the present invention.

Reference is initially made to FIG. 1, which is a schematic illustration of a system 20 for performing a cardiac ablation, in accordance with some embodiments of the present invention.

System 20 comprises a catheter 28, a proximal end of which is connected, via an electrical interface 40 (e.g., any suitable type of connector, jack, port, or plug), to a console 36, which comprises a processor 44. As described in detail hereinbelow, processor 44 receives, via electrical interface 40, electrical signals from catheter 28, processes these signals, and generates appropriate output in response thereto.

During a cardiac ablation procedure, catheter 28 is inserted by a physician 26 into the heart of a subject 24. The distal end 22 of catheter 29 comprises an ablation electrode 30, which is used to apply an ablating signal to cardiac tissue of subject 24. An ultrasound transducer 34, disposed at distal end 22 (e.g., inside ablation electrode 30), is used to transmit ultrasound signals, and receive reflections of the signals from the tissue. In response to the received reflections, ultrasound transducer 34 generates signals, which are received by processor 44. The ultrasound transducer is used for both (i) measuring tissue thickness prior to the ablation, in order to properly set the ablation parameters, and (ii) evaluate echogenic changes to the tissue caused by the ablation, in order to assess the outcome of the ablation.

In some embodiments, catheter 28 comprises a plurality of ultrasound transducers, which may be arranged within the ablation electrode in any suitable arrangement. For example, the ultrasound transducers may be distributed around the circumference of the ablation electrode, at the distal tip of the ablation electrode and/or proximally to the distal tip. Such a plurality of ultrasound transducers may be used to transmit ultrasound signals from multiple locations, and/or in multiple directions, thus facilitating the performance of the techniques described herein.

In some embodiments, distal end 22 further comprises one or more temperature sensors 38, which may be used to record the temperature of the tissue during the ablation. Temperature sensors 38 generate signals indicative of the recorded temperatures, and communicate these signals to processor 44.

Catheter 28 further comprises a force sensor 32, which may alternatively be referred to as a pressure sensor, at the distal end of the catheter. In some embodiments, force sensor 32 operates as described in US Patent Application Publication 2009/0093806, whose disclosure is incorporated herein by reference. Force sensor 32 is configured to generate a signal that indicates both the magnitude and the direction of the mechanical force that is applied to the tissue by the distal end of the catheter.

Typically, system 20 further comprises an electromagnetic tracking system, which tracks the position and orientation of the distal end of the catheter during the procedure, as described, for example, in U.S. Pat. No. 8,456,182, whose disclosure is incorporated herein by reference.

Typically, console 36 further comprises a display 42, which displays appropriate output for the physician during the procedure. For example, display 42 may show an electroanatomical map of the subject's heart, constructed, for example, using techniques described in U.S. Pat. No. 6,226,542, whose disclosure is incorporated herein by reference. Alternatively or additionally, display 42 may be driven by processor 44 to show output from the processing of signals received from ultrasound transducer 34 and force sensor 32, as described in detail hereinbelow.

One commercial product embodying elements of system 20 is the CARTO® 3 System, available from Biosense Webster, Inc., 3333 Diamond Canyon Road, Diamond Bar, Calif. 91765. This system may be modified by those skilled in the art to embody the principles of embodiments described herein.

In general, processor 44 may be embodied as a single processor, or a cooperatively networked or clustered set of processors. Processor 44 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
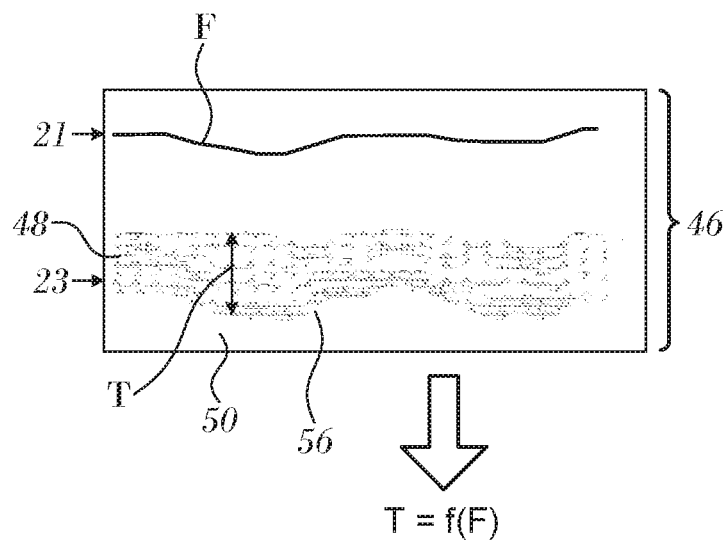
FIG. 2 is a schematic illustration of a visual output that includes a force signal and an m-mode ultrasound image, which may be displayed on a display in accordance with some embodiments of the present invention.

Reference is now made to FIG. 2, which is a schematic illustration of a visual output 46 that includes a force signal 21 and an m-mode ultrasound image 23, which may be displayed on display 42 (e.g., overlaid over a displayed electroanatomical map) in accordance with some embodiments of the present invention.

Upon inserting the catheter into the subject's heart, the physician presses the distal end of the catheter against the cardiac tissue. Typically, due to movement of the tissue over the course of the cardiac cycle, the force with which the catheter presses against the tissue varies. Alternatively or additionally, the physician may manually vary the contact force, and/or a linear actuator (not shown) incorporated into the distal end of the catheter may vary the contact force, as described, for example, in US Patent Application Publication 2016/0183915, whose disclosure is incorporated herein by reference. While the contact force varies, the ultrasound transducer transmits ultrasound signals into the tissue, and receives reflections of the signals from the tissue.

Processor 44 receives, from force sensor 32, a force signal 21, which indicates the time-varying contact force "F" applied to the tissue. Processor 44 further receives, from the ultrasound transducer, one or more signals that are derived from ultrasound reflections received by the ultrasound transducer. Such signals from the ultrasound transducer may be used to generate an m-mode ultrasound image 23 of the tissue, which shows the portion 48 of tissue that is in front of the ultrasound transducer. Assuming a large-enough contrast between tissue portion 48 and the adjacent anatomical portion 50 of the subject, image 23 allows the thickness T of tissue portion 48 to be visualized. In particular, it may be seen that T is a function of the contact force F. As the contact force increases, the tissue becomes more compressed, and hence, the thickness decreases; conversely, as the force decreases, the tissue thickness increases.

In some embodiments, at least some tissue thicknesses may be measured manually (e.g., by the physician) from image 23, and/or from the displayed electroanatomical map of the subject's heart. Typically, however, the thicknesses are obtained automatically by the processor, based on the times-of-flight of the ultrasound reflections received from the tissue. In cases in which reflections are received from multiple tissue interfaces, the processor may use techniques described in US Patent Application Publication 2016/0183915, whose disclosure is incorporated herein by reference, to identify the reflections from the tissue interface 56 of interest. In brief, the aforementioned '915 publication describes correlating force signal 21 with the time-varying times-of-flight of the received reflections. The times-of-flight from tissue interface 56 will be highly correlated with force signal 21, while those from other tissue interfaces will be less correlated. That is, as the applied force increases, thus causing the distance from the ultrasound transducer to tissue interface 56 to decrease, the times-of-flight from tissue interface 56 will decrease, and vice versa, whereas other times-of-flight will be less correlated with force signal 21. Consequently, the processor may obtain the time-varying distance from the ultrasound transducer to tissue interface 56, which is the desired tissue thickness.

Subsequently, given the time-varying contact force and the time-varying tissue thickness, the dependency of the thickness on the contact force is learned. That is, processor 44 learns "T=f(F)," which is the tissue thickness expressed as a function of the contact force. This dependency—as learned, stored, and subsequently used by the processor—may be embodied in any suitable form, such as in the form of a lookup table of corresponding "T" and "F" values, and/or in the form of parameters derived by fitting a function to the acquired "T" and "F" values.

Typically, the dependency of the tissue thickness on the contact force is learned for each of a plurality of portions of tissue. That is, as the physician moves the catheter along the tissue, force signal 21, and the signals based on the ultrasound reflections, are received, and are used to learn the dependency for each of the portions of tissue over which the catheter moves. Typically, the dependencies are first learned for a local area of an intended ablation site, an ablation is then performed at the local area, and then the catheter is moved to the next intended ablation site. In other embodiments, the learning is first performed for all of the intended ablation sites, and only afterwards are each of the sites ablated.

As indicated in FIG. 2 and described above, force signal 21 and image 23 are typically displayed on display 42. (Although, as described above, force signal 21 typically includes both the magnitude and direction of the force, the display of force signal 21 may indicate only the magnitude of the force, expressed, for example, in units of weight, such as grams.) Alternatively, processor 44 may learn the dependency of the tissue thickness on the contact force, even without any signals or images being displayed on the display.

Figure 3:
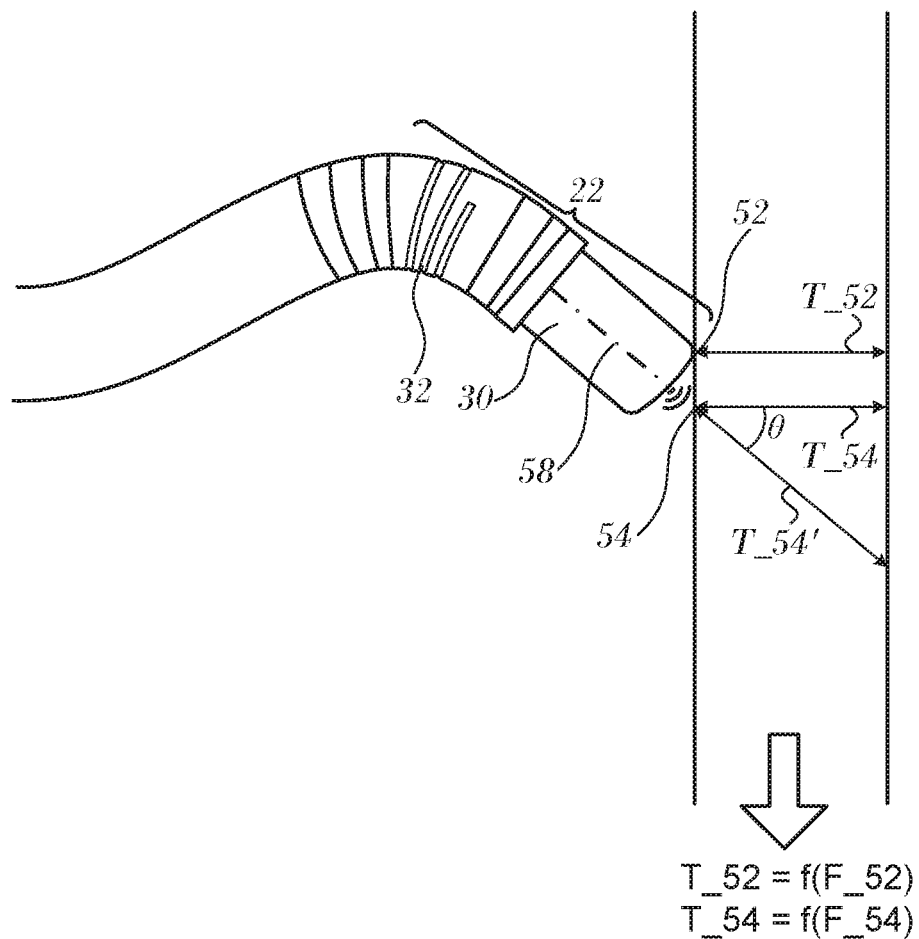
FIG. 3 is a schematic illustration of a method for ascertaining thickness of tissue, in accordance with some embodiments of the present invention.

Reference is now made to FIG. 3, which is a schematic illustration of a method for ascertaining thickness of tissue, in accordance with some embodiments of the present invention.

If distal end 22 of the catheter is perpendicular to the tissue during the acquisition of the force signal and the ultrasound reflections, the ultrasound reflections will be received from the portion of tissue to which force is being applied. On the other hand, if, as depicted in FIG. 3, the distal end of the catheter is not perpendicular to the tissue, the ultrasound transducer will face away from the portion of tissue that the catheter is pressing against, and consequently, the force signal and the ultrasound-reflection signals may not correspond to the same portion of tissue. For example, in FIG. 3, the catheter contacts a first portion 52 of tissue, but ultrasound reflections are received from a second portion 54 of tissue.

Hence, typically, the processor is configured to determine, based on the directionality of the force signal, the portion of the tissue from which the ultrasound signals were received. (The directionality of the force signal is captured by the bending of force sensor 32, as depicted in FIG. 3.) If the portion of tissue from which the ultrasound signals were received is not the currently-contacted portion of tissue, the processor selects, as the one or more ultrasound-reflection-based signals, signals derived from ultrasound reflections received during a different period of time.

For example, in the case depicted in FIG. 3, the ultrasound-reflection-based signals correspond to tissue portion 54, rather than to portion 52. Therefore, to learn the dependency for tissue portion 52, the processor selects ultrasound-reflection-based signals that correspond to tissue portion 52, these signals being acquired prior to or following the acquisition of the force signal for tissue portion 52. The processor similarly uses the correct set of signals to learn the dependency for tissue portion 54. FIG. 3 thus shows two learned dependencies: T_52=f(F_52) for tissue portion 52, and T_54=f(F_54) for tissue portion 54. (Although, in FIG. 3, ablation electrode 30 is not perpendicular to tissue portion 54, a suitable estimation technique may be used to estimate, based on the received ultrasound-reflection-based signals, the thickness of tissue portion 54. For example, T_54 may be calculated by multiplying the tissue thickness T_54', which is estimated based on the received ultrasound reflections, by the cosine of the appropriate angle theta ($\theta$), which may be ascertained from the force sensor.)

The above description assumes that ultrasound signals transmitted from ablation electrode 30 are generally transmitted from the ablation electrode in the direction of the central longitudinal axis 58 of the ablation electrode. As noted above, in some embodiments, a plurality of ultrasound transducers may be used to transmit ultrasound signals from multiple locations, and/or in multiple directions, such that, in the scenario depicted in FIG. 3, T_52 may be measured, despite the ablation electrode not being perpendicular to the tissue.

Subsequently to learning the dependency of the tissue thickness on the contact force for a particular portion of tissue, the learned dependency is used to set one or more ablation parameters for the ablation of the portion of tissue. In some embodiments, processor 44 first estimates, using the learned dependency, the thickness of the portion of tissue that would result from the desired ablation contact force (which is typically in the range of 5-30 grams) being applied to the portion of tissue. Then, in response to the estimated thickness, the processor generates an output indicating at least one recommended parameter for the ablation. For example, the output may indicate a recommended power, and/or a recommended duration, of the ablating signal. Typically, the processor displays such an output on display 42, and the physician, in response to viewing the output on the display, then sets the ablation parameters accordingly.

In other embodiments, the processor does not explicitly estimate the thickness of the portion of tissue; rather, the processor ascertains the recommended parameter directly from the desired ablation contact force. For example, given the learned dependency T=f(F), and another function A=g(T) that specifies the dependency of the recommended ablating-signal amplitude "A" on the tissue thickness, the processor may, for a particular contact force F0, ascertain the recommended amplitude A0 in either one of the following two ways:

(i) The processor may first calculate T0=f(F0) (thus explicitly using the learned dependency), and then calculate A0=g(T0).

(ii) The processor may first derive a function A=g(f(F))=h(F), and then apply this derived function (thus implicitly using the learned dependency) to ascertain A0 from F0.

In some embodiments, alternatively or additionally to generating the output that indicates the recommended ablation parameter(s), the processor generates an output—e.g., a control signal directed to the generator that supplies the ablating signal—that automatically sets the parameter(s).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
    a catheter having a force sensor, a position sensor and an ultrasonic transducer;

an electrical interface; and a processor operatively connected to the catheter through the electrical interface, the processor configured:

to receive, via the electrical interface:

a first signal generated by the force sensor that indicates a time-varying force having a magnitude and a direction that was applied to a portion of tissue, and one or more second signals generated by the ultrasonic transducer that are derived from ultrasound reflections received from the portion of tissue corresponding to a time when the directionality of the force signal aligns with the direction of the one or more second signals generated by the ultrasonic transducer and indicative of the thickness of the portion of tissue in the direction of the time-varying force, and to learn, from the first signal and the second signals, a dependency of the thickness of the portion of tissue on the force applied to the portion of tissue.

2. The apparatus according to claim 1, wherein the processor is further configured to generate, based on the learned dependency, an output indicating at least one recommended parameter for an ablation of the portion of tissue performed at a particular contact force.

3. The apparatus according to claim 2, wherein the processor is configured to generate the output by:

based on the learned dependency, estimating a thickness of the portion of tissue that would result from the particular contact force being applied to the portion of tissue during the ablation of the portion of tissue, and in response to the estimated thickness, generating the output.

4. The apparatus according to claim 2, wherein the recommended parameter includes a power of an ablating signal.

5. The apparatus according to claim 2, wherein the recommended parameter includes a duration of an ablating signal.

6. The apparatus according to claim 1, wherein the processor is further configured to set, based on the learned dependency, at least one parameter for an ablation of the portion of tissue.

7. The apparatus according to claim 1, wherein the portion of tissue is a portion of cardiac tissue.

8. The apparatus according to claim 1, wherein the time-varying force was applied to the portion of tissue by a distal end of a catheter.

9. The apparatus according to claim 8, wherein the ultrasound reflections were received by an ultrasound transducer disposed within the distal end of the catheter.

10. The apparatus according to claim 1, wherein the processor is further configured:

to ascertain, based on a direction of the time-varying force during a first period of time during which the first signal was acquired, that ultrasound reflections received during the first period of time were not reflected from the portion of tissue, and in response thereto, to select, as the one or more second signals, one or more signals that are derived from ultrasound reflections received during a second period of time that is different from the first period of time.

11. A method, comprising:

receiving a processor operatively connected to a catheter through an electrical interface, the catheter having a force sensor, a position sensor and an ultrasonic transducer:

a first signal from the force sensor that indicates a time-varying force having a magnitude and a direction that was applied to a portion of tissue, and one or more second signals from the ultrasonic transducer that are derived from ultrasound reflections received from the portion of tissue corresponding to a time when the directionality of the force signal aligns with the direction of the one or more second signals generated by the ultrasonic transducer and indicative of the thickness of the portion of tissue in the direction of the time-varying force;

learning, from the first signal and the second signals, a dependency of a thickness of the portion of tissue on the force applied to the portion of tissue; and generating an output that is based on the learned dependency.

12. The method according to claim 11, wherein the output indicates at least one recommended parameter for an ablation of the portion of tissue performed at a particular contact force.

13. The method according to claim 12, wherein generating the output comprises:

based on the learned dependency, estimating a thickness of the portion of tissue that would result from the particular contact force being applied to the portion of tissue during the ablation of the portion of tissue, and in response to the estimated thickness, generating the output.

14. The method according to claim 12, wherein the recommended parameter includes a power of an ablating signal.

15. The method according to claim 12, wherein the recommended parameter includes a duration of an ablating signal.

16. The method according to claim 11, wherein the output sets at least one parameter for an ablation of the portion of tissue.

17. The method according to claim 11, wherein the portion of tissue is a portion of cardiac tissue.

18. The method according to claim 11, wherein the time-varying force was applied to the portion of tissue by a distal end of a catheter.

19. The method according to claim 18, wherein the ultrasound reflections were received by an ultrasound transducer disposed within the distal end of the catheter.

20. The method according to claim 11, further comprising:

ascertaining, based on a direction of the time-varying force during a first period of time during which the first signal was acquired, that ultrasound reflections received during the first period of time were not reflected from the portion of tissue, and in response thereto, selecting, as the one or more second signals, one or more signals that are derived from ultrasound reflections received during a second period of time that is different from the first period of time.

* * * * *